(12) United States Patent  (10) Patent No.: US 8,579,820 B2
Jackson  (45) Date of Patent: Nov. 12, 2013

(54) FETAL HEART MONITORING

(75) Inventor: Roy Jackson, South Glamorgan (GB)

(73) Assignee: Huntleigh Technology Limited (GB)

( * ) Notice: Subject to any disclaimer, the term of this patent is extended or adjusted under 35 U.S.C. 154(b) by 216 days.

(21) Appl. No.: 13/120,248

(22) PCT Filed: Sep. 16, 2009

(86) PCT No.: PCT/GB2009/051198
§ 371 (c)(1),
(2), (4) Date: Mar. 22, 2011

(87) PCT Pub. No.: WO2010/035022
PCT Pub. Date: Apr. 1, 2010

(65) Prior Publication Data
US 2011/0172540 A1  Jul. 14, 2011

(30) Foreign Application Priority Data

Sep. 23, 2008 (GB) .................................. 0817389.0

(51) Int. Cl.
*A61B 8/02* (2006.01)
(52) U.S. Cl.
USPC ........... 600/453; 600/454; 600/455; 600/456; 600/457; 600/511
(58) Field of Classification Search
USPC .......................................... 600/453–457, 511
See application file for complete search history.

(56) References Cited

U.S. PATENT DOCUMENTS

| 4,573,479 A | 3/1986 | Tuccillo |
| 4,984,576 A | 1/1991 | Schulenberg et al. |
| 5,509,416 A | 4/1996 | Wilmott |

FOREIGN PATENT DOCUMENTS

| EP | 0657137 A1 | 6/1995 |
| GB | 2220487 A | 1/1990 |

OTHER PUBLICATIONS

Kraft et al. "Software-gated pulse-Doppler ultrasound for a DSP-based blood flowmeter" 2000 IEEE International Conference on Acoustics, Speech, and Signal Processing Proceedings. vol. 6, pp. 3598-3601.*

* cited by examiner

*Primary Examiner* — Long V. Le
*Assistant Examiner* — Colin T Sakamoto
(74) *Attorney, Agent, or Firm* — Craig A. Fieschko, Esq.; DeWitt Ross & Stevens S.C.

(57) ABSTRACT

A transmit amplifier (12) drives an ultrasound transducer (11) to emit a pulse, and a receive amplifier (13) amplifies the echo signal detected by the transducer. The receive amplifier's gate opens a fixed delay after the end of the transmit pulse, and a demodulator (14) multiplies the received signal by the local oscillator signal. A low-pass filter removes the sum of the frequencies and passes the difference of the frequencies (the received signal's Doppler frequency) to be digitized by an ADC. ADC readings are made for each of several range bins in intervals during the receive gate-open interval. One or two of the Doppler audio signals will contain the signal from the fetal heart. When a periodic signal is found, its rate is tested to see if it lies within or outside the typical range of a fetal heart.

20 Claims, 5 Drawing Sheets

FETAL HEART MONITORING

FIELD OF THE INVENTION

The present invention relates to a method of monitoring heart rate, in particular the heart rate of a fetus. Ultrasound is used to monitor the fetal heart by means of a transducer in contact with the maternal abdomen. Echoes from the fetal heart are processed so that heart sounds can be heard, and analysed to determine fetal heart rate.

BACKGROUND OF THE INVENTION

Doppler ultrasound fetal heart rate monitors insonate the fetal heart and surrounding tissue with high frequency sound. Echoes from internal tissues undergo Doppler shift proportional to the relative velocity of reflecting surface and transducer. The received ultrasound is demodulated to convert the Doppler signal to the audible range; it gives reassurance when the fetal heart can be heard in this way. Filters are used to reject signals from stationary and slowly moving tissue, and a processing algorithm is used to determine the time of occurrence of each heart beat and therefore the heart rate.

Such monitors suffer from conflicting requirements. For ease of use and versatility, the beam should be as wide as possible and penetrate to a great depth. However, for robust FHR detection, the sensitive region of the beam needs to be limited to a small volume around the fetal heart, rejecting echoes from other organs and moving tissue. Particularly problematic sources of unwanted echoes include fetal limbs, maternal blood vessels, the digestive tract, and in the case of multiple pregnancies, a sibling of the target fetus.

Furthermore, when the transducer moves slightly in relation to the mother's abdomen, typically when the mother changes position, large Doppler reflections are received from every point within the ultrasound beam. Such movement artefact is normally many times larger than the fetal signal and disrupts or confounds the extraction of fetal heart rate.

Some monitors use pulsed Doppler ultrasound which improves the signal-to-noise ratio (SNR) by gating the ultrasound receiver such that it only accepts signals within a certain range of times after the ultrasound pulse is transmitted. The opening and closing times of the gates are chosen to correspond to a desired transit time for the ultrasound and thus determine a maximum and minimum operating range for the ultrasound beam. Echoes from near tissues arrive too early to be detected while distant echoes arrive too late. Timing of the receive gate may be fixed or may vary under control of an algorithm in order to collect echoes from the locality of the fetal heart while rejecting unwanted echoes from other ranges.

Some systems offer a choice of ultrasound frequency. This is useful because attenuation of ultrasound in tissue is proportional to frequency, the sound from a lower frequency transducer penetrating to a greater depth than a higher frequency. Therefore, the user will select a low frequency when they require greatest range (for example with an overweight mother) but will select a higher frequency to avoid picking up unwanted echoes from deep organs or tissue in a slimmer mother.

Systems having fixed, wide receive gates may have difficulty extracting an accurate fetal heart rate when the signal contains a mixture of echoes from maternal blood vessels and fetal heart. This is especially problematic when the beam is not well-aimed at the fetal heart and the fetal signal is smaller or similar in amplitude to the maternal signal.

Systems with adaptive receive gate timing are able to narrow down the receive gate and track the fetal heart (at least in one dimension—the distance from the transducer) which gives them a better SNR than systems having a fixed, wide receive gate. This strength can also be a weakness however. By locking on to a signal source and ignoring signals from other depths, it is possible for the system to erroneously lock on the wrong signal; most commonly this would be a maternal blood vessel. For example, in a prior art system as shown in FIG. 1, the transducer (2) is incorrectly positioned on the maternal abdomen (1) such that the beam (3) does not insonate the fetal heart (6). The maternal descending aorta (4) is within the beam (3) and the system detects maternal heart rate because it is the only periodic signal available to it. Believing it has a valid fetal signal, the system narrows down it's receive gate until the sensitive volume is limited to the region (5). Even when the transducer is subsequently moved to the correct position as shown in FIG. 2, the system does not detect the fetal heart (6) although it is now in the beam (3) because the heart is not inside the sensitive region (5). This erroneous state could persist indefinitely.

The present invention aims to make improvements.

SUMMARY OF THE INVENTION

Accordingly, the present invention provides fetal heart monitoring system using ultrasound having a single receive circuit with a single, fixed, wide receive gate with the output being digitised repeatedly by an analogue-to-digital converter (ADC) during the gate-open interval with each digital value assigned to one of several range bins.

Preferably, each range bin is arranged to accept a single ADC sample.

More preferably, two or more ADC samples are assigned to each bin, the samples within each bin processed using standard noise reduction techniques to produce a single signal within each bin.

Advantageously, a different gain is applied to each range bin in order to simulate the attenuation characteristic of a higher frequency transducer. This allows the user to select the effective penetration profile of the ultrasound beam without having to bear the cost of additional transducers. This ability is not limited to mimicking probes of other frequencies, it is possible to produce any arbitrary attenuation profile.

Alternatively, the sensitivity individually in the range bins is adjusted by adjusting the threshold required for a signal to be detected or by applying different weightings to each range bin. This has the advantages of not degrading the signal by attenuating it, and being computationally more efficient.

Preferably, the range bins are recombined in pairs, trios, or groups of any number to recreate the composite signal corresponding to the depth range of those bins.

Preferably, the range bins are recombined after applying an individual attenuation factor to each bin to simulate the use of a higher ultrasound frequency or create an arbitrary attenuation profile.

In a preferred embodiment, the amplitudes of the signals in all the range bins are compared to detect any sudden rise in amplitude across all the range bins showing the presence of artefact caused by transducer movement.

Preferably, the amplitude of the artefact is detected as a numerical value rather than a simple on/off indication. Such numerical value can be used as the controlling variable in an automatic gain circuit (AGC) implemented either in hardware or in software. This has the advantage of reducing the sensitivity of the circuits or algorithms during artefact causing less disruption to the heart rate detection process. Without such ACG, artefact signals are one or two orders of magnitude larger than typical fetal signals and can confuse the rate detection process by overloading filters or circuits and altering thresholds which require some time to recover. With ACG, the artefact is either attenuated or removed entirely and the recovery time is shortened.

Preferably, the volume of the Doppler signal is modulated during artifact. Artefact is typically much louder than fetal sounds and can be disturbing to hear, and can cause clipping and distortion in the audio amplifier. By reducing the volume during artefact, the audio output is maintained at a comfortable level and has a more pleasant tone.

BRIEF DESCRIPTION OF THE DRAWINGS

Preferred embodiments of the invention will now be described with reference to the following Figures, of which.

DETAILED DESCRIPTION OF PREFERRED VERSIONS OF THE INVENTION

Figure 1:
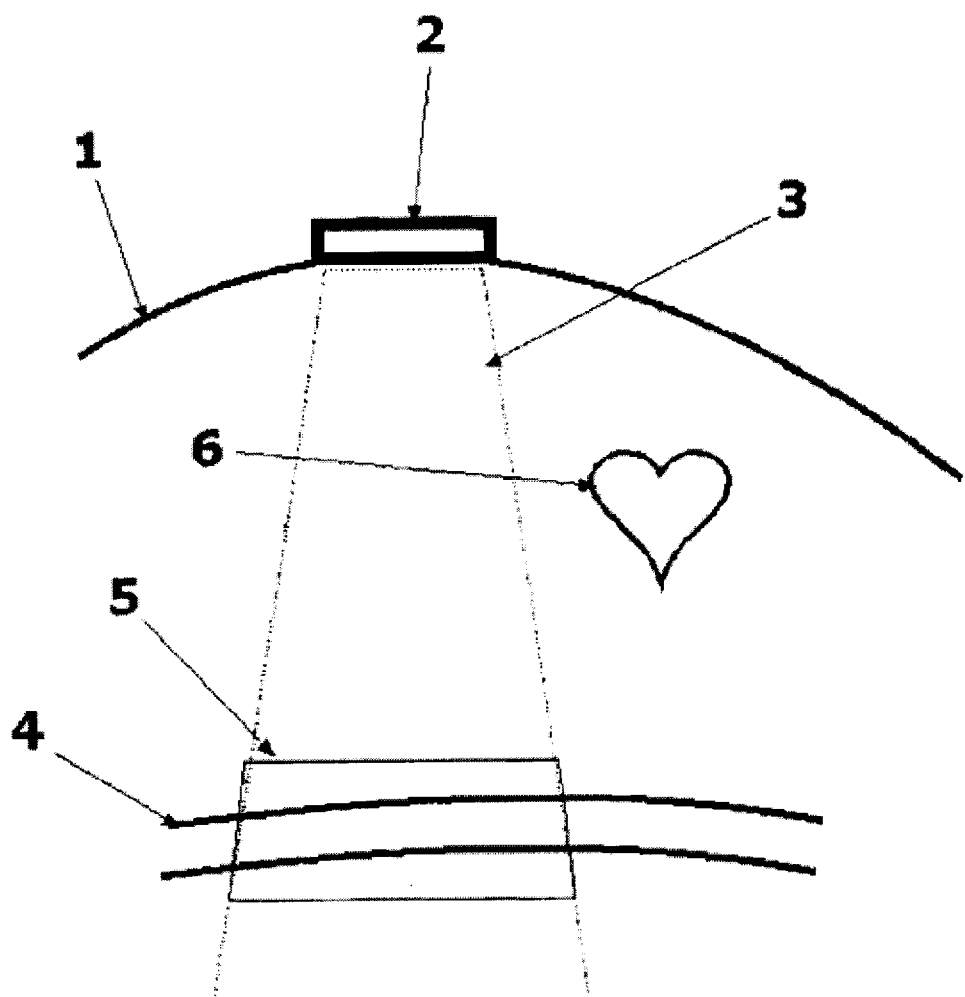
FIG. 1 shows a prior art fetal heart monitoring system.
Figure 2:
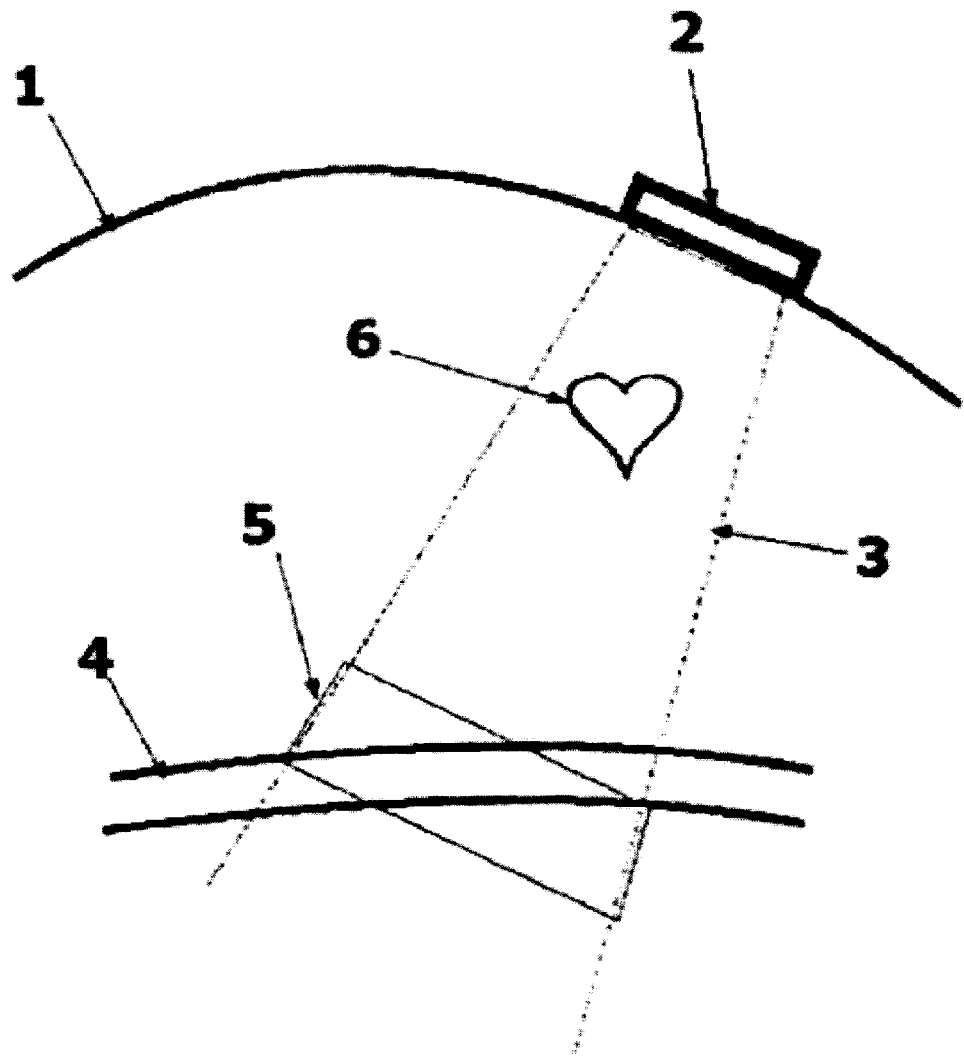
FIG. 2 shows the monitoring system in FIG. 1 with the receive gate in the wrong position.
Figure 3:
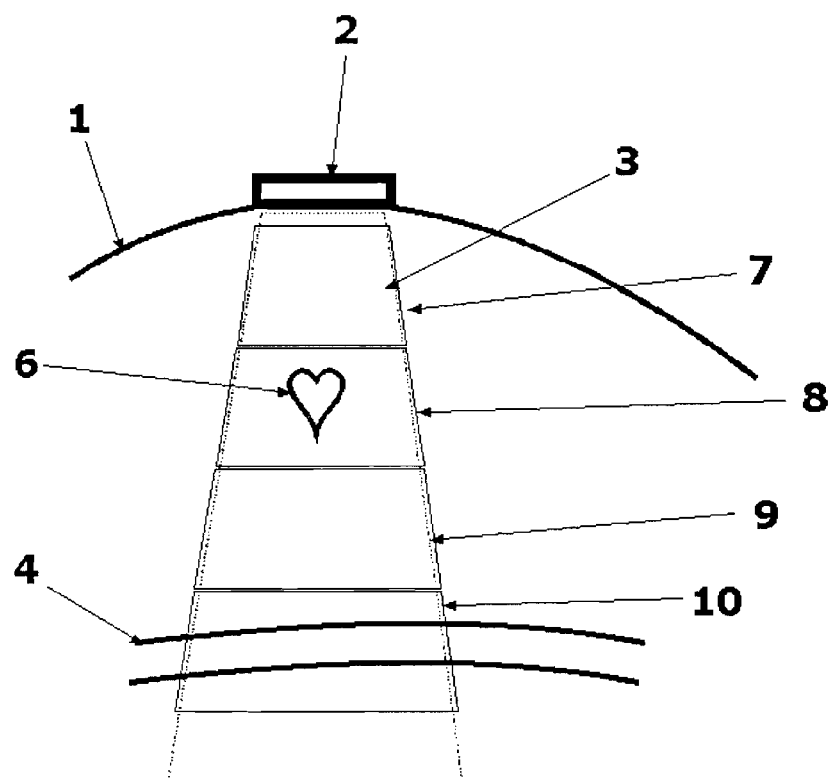
FIG. 3 shows a fetal monitoring system according to the invention.

Referring to FIG. 3, the present invention uses multigating where the beam is zoned into four sensitive regions, although more or fewer is possible. The zones (7, 8, 9, 10) are shown non-overlapping for clarity, but by selection of the appropriate open and close times for each gate and taking into account the duration of the transmit pulse, the zones could be made to overlap to any desired extent, or indeed to have gaps between them.

In this example, one received signal is split into four components, each from a different depth. As with adaptive range-gating, each signal benefits from reduced noise level because it originates from a smaller volume. Gates 1 & 3 (7 & 9) contain only aperiodic noise. Gates 2 & 4 (8 & 10) contain periodic signals from which can be deduced fetal and maternal heart rates. Standard heart rate algorithms are able to extract both rates simultaneously and without confusion since the signals have already been separated spatially. Further processing is required to determine which signal is from the fetus; this can be decided on several criteria such as depth and signal amplitude.

The present invention also incorporates a simplification to the arrangement described above. The cost of replicating the input analogue circuits for each range gate is not insignificant and mitigates against using a large number of gates. However, the same effect can be achieved by using a single receive circuit with a single, fixed, wide receive gate with the output being digitised repeatedly by an analogue-to-digital converter (ADC) during the gate-open interval. Each digital value is assigned to one of several range bins.

In the simplest case, each range bin would accept a single ADC sample. However, SNR can be further improved by assigning two or more ADC samples to each bin. The samples within each bin are processed using a standard noise reduction technique such as filtering, averaging, etc. to produce a single signal within each bin.

Figure 4:
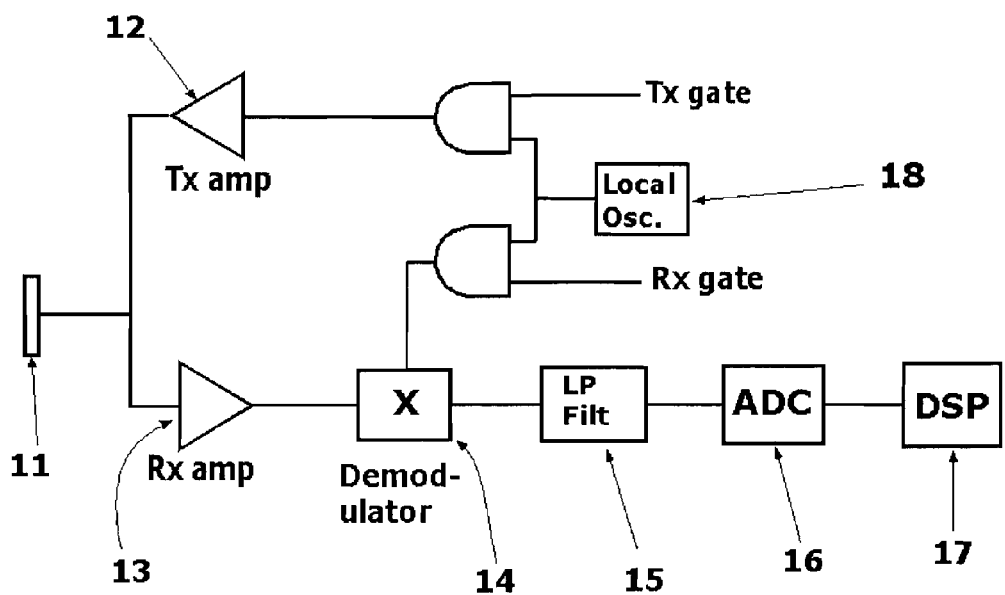
FIG. 4 shows a preferred embodiment of the invention.

In a preferred embodiment of the invention, as shown in FIG. 4, the transducer (11) is driven by transmit amplifier (12) with a tone burst of 1 MHz carrier from the local oscillator (18). The pulse duration is 64 µs and the repetition rate is 3 kHz. Receive amplifier (13) amplifies the echoes detected by the transducer. The receive amplifier may be blanked during the transmit pulse, but this is not necessary, provided the receive amplifier recovers sufficiently quickly once the pulse is over. While the receive gate is open, demodulator (14) multiplies the received signal by the local oscillator signal. The output is the sum and difference frequencies. The sum, which is approximately 2 MHz, is removed by low-pass filter (15), while the difference is the Doppler frequency of the received signal which passes through the filter to be digitised by ADC (16).

Figure 5:
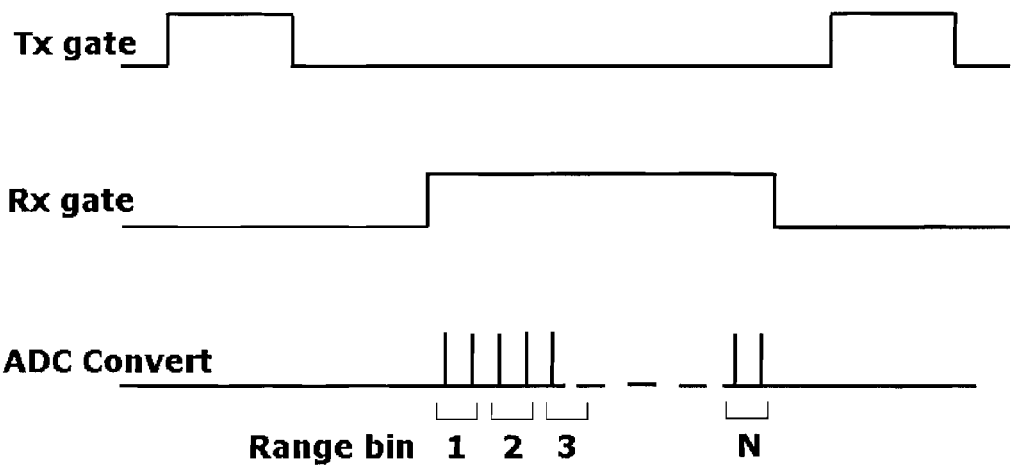
FIG. 5 shows the opening and closing of the receive gates according to the embodiment in FIG. 4.

Timing of the ADC conversions is important. FIG. 5 shows the Rx gate opening a fixed delay after the end of the transmit pulse. This time determines the closest signal source that can be detected. Similarly, the closing of the Rx gate determines the most distant signal source that can be detected. Within the Rx gate, a series of A to D conversions is made, timed by the convert command signal. In a specific example of the invention, the number of range bins is 6 and two ADC readings are needed for each bin. Twelve ADC readings are made at 16 µs intervals during the Rx gate-open interval. To reduce noise, the two readings in each bin are averaged. In the example, this operation is carried out by a hardware adder circuit, although it could equally well have been done in software.

Because the transmit pulse is equal in duration to two range bins, the sensitive regions of adjacent bins overlap. A single point source will therefore always appear in two adjacent bins. Although this is not an essential part of the invention, in this example, it is now possible to further improve SNR ratio by combining together the signals in adjacent pairs of bins, producing a total of five combined signals from six bins. Specifically, the first combined signal is derived by combining bins 1 & 2, the second combined signal is derived from bins 2 & 3, etc. In the example, this operation is carried out in software, although it could equally well have been done in hardware.

At this point in the system, there are 5 Doppler audio signals of which one or possibly two will contain the signal from the fetal heart. The others will contain unwanted signals that may be aperiodic or periodic. Each signal is processed in the same way, using methods that are typical in ultrasound heart rate detectors: signals are band-pass filtered, rectified and enveloped. An algorithm seeks periodic activity in the enveloped signal using typical standard techniques such as peak-detection, auto-correlation, matched-filtering, etc. When a periodic signal is found, its rate is tested and rejected if it lies outside the typical range of a fetal heart (30 to 250 beats per minute). For each acceptable rate that is found a quality factor is calculated in a way that is typical of ultrasound heart rate monitors, based on criteria including amplitude, steadiness of rate, duration of rate, background noise level, or presence of artefactc. Decision logic compares the outputs of each rate detector and presents to the user the best rate according to the quality factor.

Unwanted artefact on signals is removed before the heart rate detection process as follows. Each of the 6 range bin signals is full-wave rectified and low-pass filtered with a time constant of a few ms. This produces a measure of the quasi-instantaneous amplitude of each signal, which is sampled at a rate of 75 Hz. A further low-pass filter with a time constant of several seconds calculates the longer-term average amplitude of the signal in each range bin. The ratio of quasi-instantaneous amplitude to long-term amplitude is a measure of the changeability of the signal. For a typical fetal heart signal the value of changeability is in the range 2 to 4. Random white noise has a changeability of approximately one. Signals that change rapidly in amplitude have higher values of changeability. In the artefact detector, the product of 6 changeability values is calculated. With a fetal heart in two adjacent bins and noise in the other four, the normal value of the product is below 16. However, when the transducer is moved, all range bins see a sudden increase in amplitude and the changeability product increases markedly; values of many hundreds, or more often many thousands are seen. This is therefore a very sensitive test for artefact. An artefact flag is set when the changeability product exceeds a suitable threshold, somewhere in the range 16 to 1000 being appropriate.

False positive artefact detections can be triggered by noise spikes on the data. These are removed by a morphological filter (circular, 100 ms, bottom filter) such that only sustained artefact is detected.

The gain of the enveloped Doppler signals input to the rate detection process is reduced according to the height of the artefact signal above the threshold. In this way, Doppler signals that are free from artefact are unchanged but those that trigger the artefact detector are reduced proportionately. Even a relatively weak artefact indication of several hundred is sufficient to reduce the artefact signal to below the noise floor of the system, fully protecting the rate detectors from the disturbance. In practice, a short delay occurs in the detection of artefact due to finite filter time constants and the onset of the artefact is not blanked. However, the system puts the Doppler envelope signals through a short delay chosen such that the gain reduction is perfectly aligned with the artefact.

Similarly, the audio signal is controlled by the artefact detector. Audio volume is normally set at maximum when the artefact signal is below the threshold. However, as the artefact signal increases above the threshold, gain is reduced in proportion to the height of the artefact above threshold. Unlike rate detection however, it sounds unnatural to completely silence the audio during artefact and so a minimum volume level is applied so that artefact can still be heard without being objectionably loud. Again, the artefact is detected slightly after onset due to processing delays. Compensation is applied here too; as the audio path of the system is digital, a natural delay occurs where the audio is buffered and output to a codec. The volume adjustment is fed forward directly to the codec, making up the time lost in processing so that the volume change is perfectly aligned with the artefact sound.

The invention claimed is:

1. An ultrasound fetal heart monitoring system comprising:
   an ultrasound transducer configured to generate and receive acoustic signals;
   a transmit circuit configured to drive the ultrasound transducer by generating a transmit signal having a period;
   a receive circuit configured to receive echo signals from the ultrasound transducer during a single gate-open interval in each period;
   an analogue-to-digital converter configured to digitise the echo signals from the receive circuit; and a processing unit configured to assign each digitised echo signal to one of several distance range bins by controlling the timing of digitisation of the analogue-to-digital converter within the single gate-open interval.

2. The system of claim 1 wherein the gate-open interval begins a fixed delay following generation of the transmit signal by the transmit circuit.

3. The system of claim 2 wherein:
   the gate-open interval includes a gate opening and a gate closing;
   the gate opening corresponds with a smallest depth within a maternal abdomen from which signals are received by the ultrasound transducer; and
   the gate closing corresponds with a largest depth within the maternal abdomen from which signals are received by the ultrasound transducer.

4. The system of claim 3:
   wherein the processing unit is further configured to: assign two or more consecutively digitised echo signals to each distance range bin;
      process the two or more digitised assigned echo signals to each distance range bin to produce a single signal for each range bin; and
      combine the single signals of two or more distance range bins to generate a composite signal corresponding to a depth range within the maternal abdomen.

5. The system of claim 4 wherein:
   the transmit signal includes a transmit signal start and a transmit signal end; and
   the fetal heart monitoring system is configured such that the gate-open interval lasts at least half the duration from the transmit signal end of a first transmit signal to the transmit signal start of a second transmit signal, the second transmit signal immediately following the first transmit signal.

6. The system of claim 1 wherein the fetal heart monitoring system is configured to apply different gains to at least two of the distance range bins.

7. The system of claim 1 wherein the processing unit is configured to identify two or more of the distance range bins having echo signals therein which exhibit periodic change, wherein the periodic change of the echo signals in one of the two or more distance range bins differs from the periodic change of the echo signals in the remaining two or more distance range of the bins.

8. The system of claim 1 wherein the processing unit is configured to identify two or more of the distance range bins having echo signals therein which exhibit periodic change, wherein the two or more distance range bins are spaced by at least one intermediate distance range bin.

9. The system of claim 1 wherein the fetal heart monitoring system is configured to identify motion of the transducer when all distance range bins exhibit a sudden amplitude increase.

10. The system of claim 1 wherein the fetal heart monitoring system is configured to identify motion of the transducer when a short-term average of echo signal amplitudes in at least most of the distance range bins exceeds a long-term average of echo signal amplitudes in at least most of the distance range bins by a predefined threshold magnitude.

11. The system of claim 1 wherein the fetal heart monitoring system is configured to:
   provide audio output having an amplitude which changes in dependence on the amplitudes of the echo signals, and
   downwardly adapt the amplitude of the audio output in dependence on the degree to which a short-term average of echo signal amplitudes in at least most of the distance range bins exceeds a long-term average of echo signal amplitudes in at least most of the distance range bins.

12. A method of using ultrasound to monitor a fetal heart comprising:
   driving a transducer using a transmit circuit, the transmit circuit generating a transmit signal having a period;
   receiving and amplifying echo signals received from the transducer using a receive circuit, the receive circuit having a single gate-open interval during which echo signals are received in each period;
   digitising the output of the receiver circuit using an analogue-to-digital converter to produce digitised echo signal values; and assigning each digitised echo signal value to one of several distance range bins by controlling the timing of the analogue-to-digital converter digitisations within the single gate-open interval using a processing unit.

13. The method of claim 12 wherein the gate-open interval of the receive circuit:
   is timed to begin a fixed delay following the transmit signal; and
   includes a gate opening and a gate closing,
      the gate opening controlling a smallest depth within a maternal abdomen from which transducer signals are amplified,
      the gate closing controlling a largest depth within the maternal abdomen from which transducer signals are amplified by the receive circuit.

14. The method of claim 13 further including the steps of:
   assigning two or more digitised signals to each range bin;
   processing the digitised signals in each range bin to produce a single signal within each range bin, each signal corresponding to a depth within the maternal abdomen; and
   combining the single signals of range bins into groups of two or more range bins to generate composite signals corresponding to a range of depths within the maternal abdomen.

15. The method of claim 12 further including the step of applying different gains to different ones of the distance range bins.

16. The method of claim 12 further including the step of identifying two or more of the distance range bins having periodically changing echo signals therein, wherein the periodic changes differ between at least two of the two or more distance range bins.

17. The system of claim 12 further including the step of identifying two or more of the distance range bins having periodically changing echo signals therein, wherein the two or more distance range bins are spaced by at least one intermediate distance range bin.

18. The method of claim 12 further including the step of generating a signal indicative of transducer motion when all distance range bins exhibit a sudden amplitude increase.

19. The method of claim 12 further including the step of generating a signal indicative of transducer motion when a short-term average of echo signal amplitudes in at least most of the distance range bins exceeds a long-term average echo of signal amplitudes in at least most of the distance range bins by a predefined threshold magnitude.

20. The method of claim 12 further including the steps of:
   providing audio output, wherein the amplitude of the audio output changes in dependence on the amplitudes of the echo signals, and
   downwardly adapting the amplitude of the audio output in dependence on the degree to which a short-term average of echo signal amplitudes in at least most of the distance range bins exceeds a long-term average of echo signal amplitudes in at least most of the distance range bins.

* * * * *